United States Patent [19]

Chester et al.

[11] 4,429,176
[45] Jan. 31, 1984

[54] ACTIVE ZEOLITE CATALYSTS OF IMPROVED STABILITY

[75] Inventors: Arthur W. Chester; Yung F. Chu, both of Cherry Hill, N.J.

[73] Assignee: Mobil Oil Corporation, New York, N.Y.

[21] Appl. No.: 346,440

[22] Filed: Feb. 8, 1982

[51] Int. Cl.³ .......................... C07C 1/00; C07C 1/20; C07C 1/22; C07C 5/30
[52] U.S. Cl. .................................... 585/481; 585/408; 585/410; 585/416; 585/469; 585/640; 585/733; 502/77
[58] Field of Search ............... 585/481, 408, 469, 412, 585/413,415,422,424,640,639; 252/455

[56] References Cited

U.S. PATENT DOCUMENTS

| | | | |
|---|---|---|---|
| 4,188,282 | 2/1980 | Tabak et al. | 585/481 |
| 4,224,141 | 9/1980 | Morrison et al. | 585/481 |
| 4,236,996 | 12/1980 | Tabak et al. | 585/481 |
| 4,283,584 | 8/1981 | Chester et al. | 585/481 |
| 4,324,696 | 4/1982 | Miale | 585/481 |

*Primary Examiner*—Delbert E. Gantz
*Assistant Examiner*—A. Pal
*Attorney, Agent, or Firm*—Alexander J. McKillop; Michael G. Gilman; Charles J. Speciale

[57] ABSTRACT

A zeolite of improved stability for use in acid-catalyzed reactions is prepared by mildly presteaming the catalyst under controlled conditions of temperature, time, and steam partial pressure. The resulting catalyst retains nearly the same activity as that of a fresh unsteamed catalyst.

15 Claims, 4 Drawing Figures

ACTIVE ZEOLITE CATALYSTS OF IMPROVED STABILITY

BACKGROUND OF THE INVENTION

1. Field of the Invention

This invention relates to a process for presteaming a zeolite catalyst so as to substantially retain its initial activity and to a process for the preparation of superior zeolite catalysts to be used in acid-catalyzed reactions.

2. Description of the Prior Art

Acid-catalyzed reactions, e.g. xylene isomerization, toluene disproportionation, etc., result in the rapid degeneration of catalyst activity. It is well known to the art that mild-to-severely steamed zeolite catalysts provide improved stability but suffer from lowered activity in acid-catalyzed reactions.

Much of the prior art in this area deals with severely steamed zeolite catalysts in reactions such as xylene isomerization.

U.S. Pat. No. 4,224,141 discloses a xylene isomerization process with a catalyst steamed at a temperature in excess of 1000° F. for a period of time longer than 15 hours. The resulting catalyst is highly stable, but suffers from lowered activity.

U.S. Pat. No. 4,188,282 discloses a xylene isomerization process using a catalyst with a silica/alumina ratio of at least 200. The catalyst is severely steamed to a lowered activity as described in U.S. Pat. No. 4,016,218 and U.S. Pat. No. 3,965,209.

U.S. Pat. No. 4,236,996 discloses a xylene isomerization process wherein the catalyst is steamed at a high temperature to reduce the activity such that the conversion reaction temperature must be increased by at least 50° F. to equal the conversion capability of an unsteamed zeolite.

U.S. Pat. No. 3,965,209 discloses a process whereby the zeolite is steamed to reduce the alpha activity to less than 500 by treating the zeolite in a steam atmosphere at a temperature of from 250° to about 1000° C. (526° to about 2026° F.) for from about ½ hour to 100 hours.

SUMMARY OF THE INVENTION

This invention discloses a highly siliceous zeolite catalyst of improved stability and having an activity which is substantially equal to that of a fresh unsteamed catalyst. Such a catalyst is obtained by mildly presteaming the catalyst under controlled conditions of temperature, time and steam partial pressure.

DETAILED DESCRIPTION OF THE INVENTION

This invention is accomplished by presteaming a fresh zeolite catalyst under mild conditions until the activity of the mildly steamed catalyst is substantially equivalent to that of a fresh, unsteamed catalyst.

Particularly preferred catalysts are those zeolites having a constraint index within the approximate range of 1 to 12. Zeolites characterized by such constraint indices induce profound transformations of aliphatic hydrocarbons to aromatic hydrocarbons in commercially desirable yields and are generally highly effective in conversion reactions involving aromatic hydrocarbons. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination a silica to alumina mole ratio of at least about 12; and a structure providing constrained access to the crystalline free space.

The zeolite will have a silica/alumina ratio greater than 12. The silica to alumina ratio referred to may be determined by conventional analysis. This ratio is meant to represent, as closely as possible, the ratio in the rigid anionic framework of the zeolite crystal and to exclude aluminum in the binder or in cationic or other from within the channels. Such zeolites, after activation, acquire an intracrystalline sorption capacity for normal hexane which is greater than that for water, i.e., they exhibit "hydrophobic" properties. It is believed that this hydrophobic character is advantageous in the present invention.

The type of zeolites described freely sorb normal hexane and have a pore dimension greater than about 5 Angstroms. In addition, the structure must provide constrained access to large molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Zeolites suitable for the present invention are those having a constraint index in the approximate range of 1 to 12.

| ZEOLITES | C.I. |
| --- | --- |
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-14 | 0.5 |
| H—Zeolon | 0.4 |
| REY | 0.4 |
| Amorphous Silica-Alumina | 0.6 |
| Erionite | 38 |

It is to be realized that the above constraint index values typically characterized the specified zeolites but that such are the cumulative result of several variables used in determination and calculation thereof. Thus, for a given zeolite depending on the temperatures employed within the aforenoted range of 550° F. to 950° F., with accompanying conversion between 10% to 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with probability, in some instances, of compounding variable extremes.

While the above experimental procedure will enable one to achieve the desired overall conversion of 10% to 60% for the most catalyst samples and represents preferred conditions, it may occasionally be necessary to use somewhat more severe conditions for samples of very low activity, such as those having a very high silica to alumina ratio of high sodium content. In those instances, a temperature of up to about 1000° F. and a liquid hourly space velocity of less than one, such as 0.1 or less, can be employed in order to achieve a minimum total conversion of about 10%.

The class of zeolites defined herein is exemplified by ZSM-5, ZSM-11, ZSM-12, ZSM-35, ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally it is possible (and is usual practice) to activate this type catalyst by base exchange with ammonium salts followed by calcination in air or about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-35, and ZSM-38, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired. Therefore, the preferred zeolites of this invention are those having a constraint index as defined above of about 1 to about 12, a silica to alumina ratio of at least about 12 and a dried crystal density of not less than about 1.6 grams per cubic centimeter.

The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceeding of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite may be converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been replaced by another cation may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above-described crystalline aluminosilicate zeolite in another material resistant to the temperature and other conditions employed in the process. Such matrix materials include synthetic or naturally occurring substances as well as inorganic materials such as clays, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-alumina-magnesia and silica-magnesia-zirconia. The matrix may be in the form of a cogel. The relative proportions of zeolite component and inorganic oxide gel matrix may vary widely with the zeolite content ranging from about 1 to about 99 percent by weight and more usually in the neighborhood of about 65 percent by weight of the composite.

U.S. Pat. No. 4,163,028 describes a novel method of processing $C_8$ aromatics for isomerization of xylene and conversion of ethylbenzene. According to that patent, the reactions are conducted at temperatures of 800° to 1000° F. with a zeolite having a constraint index of 1 to 12 and a very high silica/alumina ratio which may be as high as or higher than 3000. Such catalysts have low acid activity by reason of the small number of sites capable of being rendered protonic by ammonium exchange and calcination.

The improvement over the prior art is predicated upon the discovery that it is not necessary to severely reduce the activity of zeolite catalyst by steaming in order to obtain enhanced stability. It has been found that, by mildly presteaming a fresh zeolite catalyst under controlled conditions the catalyst will initially exhibit an increase in activity followed by a gradual decline. When the activity of the catalyst becomes substantially similar to that of the fresh, unsteamed catalyst, the steam treatment is terminated. The resulting catalyst has an activity level substantially similar to that of fresh, unsteamed catalyst together with improved stability.

Examples 1–10

Table 1 illustrates the effect of very mild presteaming on fresh zeolite catalyst for use in xylene isomerization. The catalyst employed in each example is HZSM-5 with a silica/alumina ratio of 70. In Table 1, $\alpha$ represents the degree of activity of the mildly steamed catalyst; $\alpha_o$ represents the degree of activity of the fresh, unsteamed catalyst, and $\alpha/\alpha_o$ represents the degree in which $\alpha$ increases over or decreases below $\alpha_o$.

TABLE 1

| | Effect of Steaming of HZSM-5 | | | | | | | | | |
|---|---|---|---|---|---|---|---|---|---|---|
| Example No. | 1 | 2 | 3 | 4 | 5 | 6 | 7 | 8 | 9 | 10 |
| Steam Treat | None | 100% | 100% | 100% | 100% | 100% | 100% | 100% | 100% | 100% |
| Hours | Fresh | 6 | 6 | 6 | 3 | 6 | 6 | 8 | 3.5 | 8 |
| Temp. °F. | Fresh | 400 | 500 | 600 | 800 | 800 | 850 | 875 | 1000 | 1025 |
| Press. psig | Fresh | 0 | 0 | 0 | 0 | 0 | 0 | 0 | 0 | 0 |
| $\alpha$ | 160* | 240 | 380 | 360 | 148 | 130 | 82 | 60 | 33 | 20 |
| $\alpha/\alpha_o$ | 1 | 1.5 | 2.4 | 2.3 | 0.9 | 0.8 | 0.5 | 0.4 | 0.2 | 0.1 |

*$\alpha = \alpha_o$

As is well known in the art, the $\alpha$-activity gives an approximate indication of the catalytic cracking activity of the catalyst compared to a standard catalyst and it gives the relative rate constant (rate of normal hexane conversion per volume of oxide composition per unit time). It is based on the activity of the highly active silica alumina cracking catalyst taken as an $\alpha$ of 1. This test is described in U.S. Pat. No. 3,354,078 and in *The Journal of Catalysis*, Vol. 4, pp. 522–529, August 1965. For purposes of the present invention, however, all measurements of $\alpha$ are to be made at 1000° F., and all references to $\alpha$ are to be understood to refer to the value obtained when the hexane cracking is measured at 1000° F.

BRIEF DESCRIPTION OF DRAWINGS

Illustrated in FIG. 1 is the relationship of activity of the mildly presteamed catalyst to the steaming severity of the catalyst. The parameters for steaming severity are represented in Table 1. It is understood that the term "steaming severity" represents a proportional relationship between the length of time, the temperature, the partial pressure and the percent steam in the steam treatment. As is shown in FIG. 1, an increase in steaming severity resulted in an increase in $\alpha$-activity of the catalyst to a point of peak enhancement (represented by Example 3, Table 1). With continued increases in steaming severity, the $\alpha$-activity decreased. At the level of severity represented by Example 5, Table 1, the $\alpha$-activity of the catalyst was substantially equivalent to that of the fresh catalyst ($\alpha = 0.9\alpha_o$). As can be readily seen from Examples 7–10, increased steaming severity further diminished the $\alpha$-activity of the zeolite catalyst.

The import of mildly presteaming a zeolite catalyst is disclosed in FIG. 2 which illustrates the relative cycle lengths of fresh and presteamed catalysts in xylene isomerization reactions. Under similar isomerization conditions, the presteamed catalysts ($\alpha = 148$) continued to operate at least 3 times longer per run. As the steaming severity increased (Examples 6–10), the resultant catalysts demonstrated increased stability. However, as is shown in Table 1, the catalyst activity diminished. Thus, mildly steaming a fresh zeolite catalyst under conditions such that the steaming conditions result in a catalyst having an $\alpha$-activity no less than 75% and, preferably, greater than 85% of the activity of a fresh unsteamed catalyst and with greatly enhanced stability is desired for the present invention.

Examples 11–15

Figure 1:
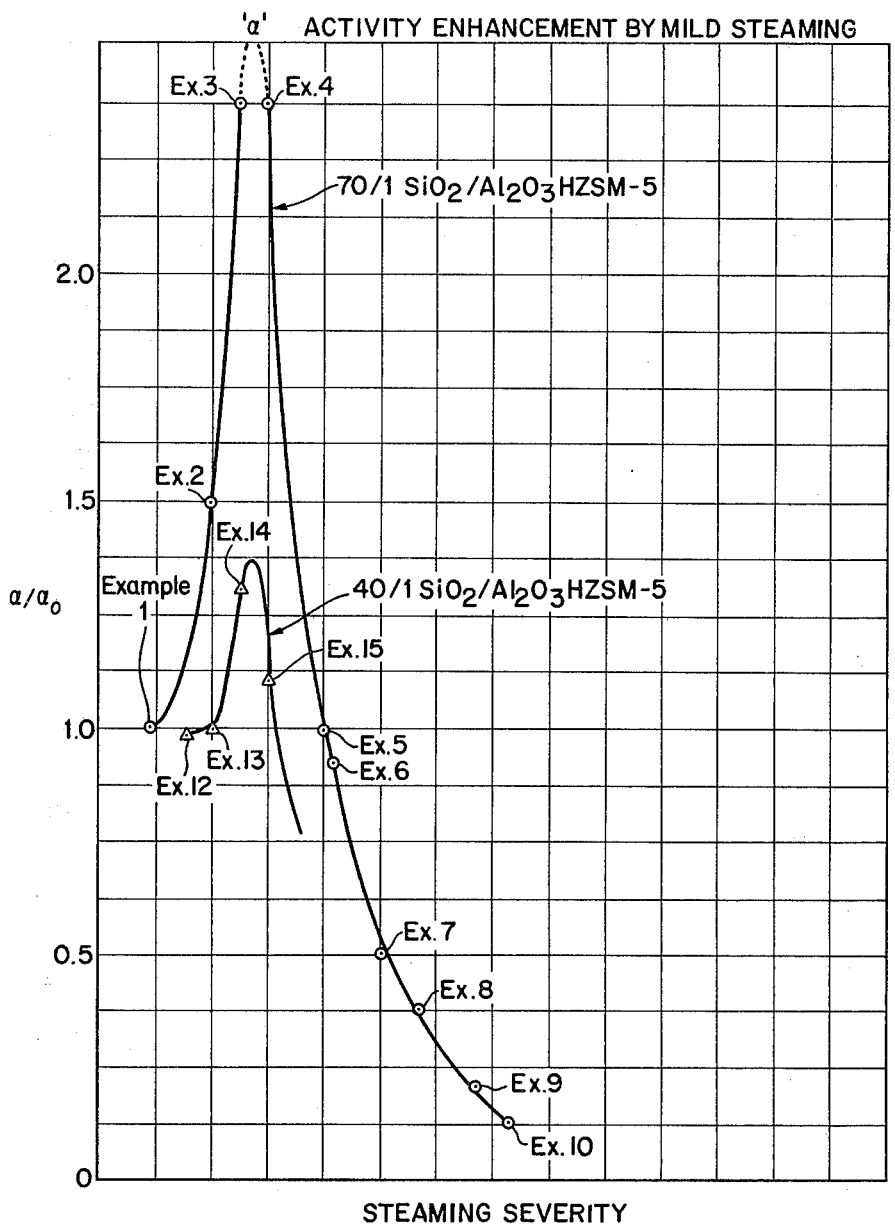
Figure 2:
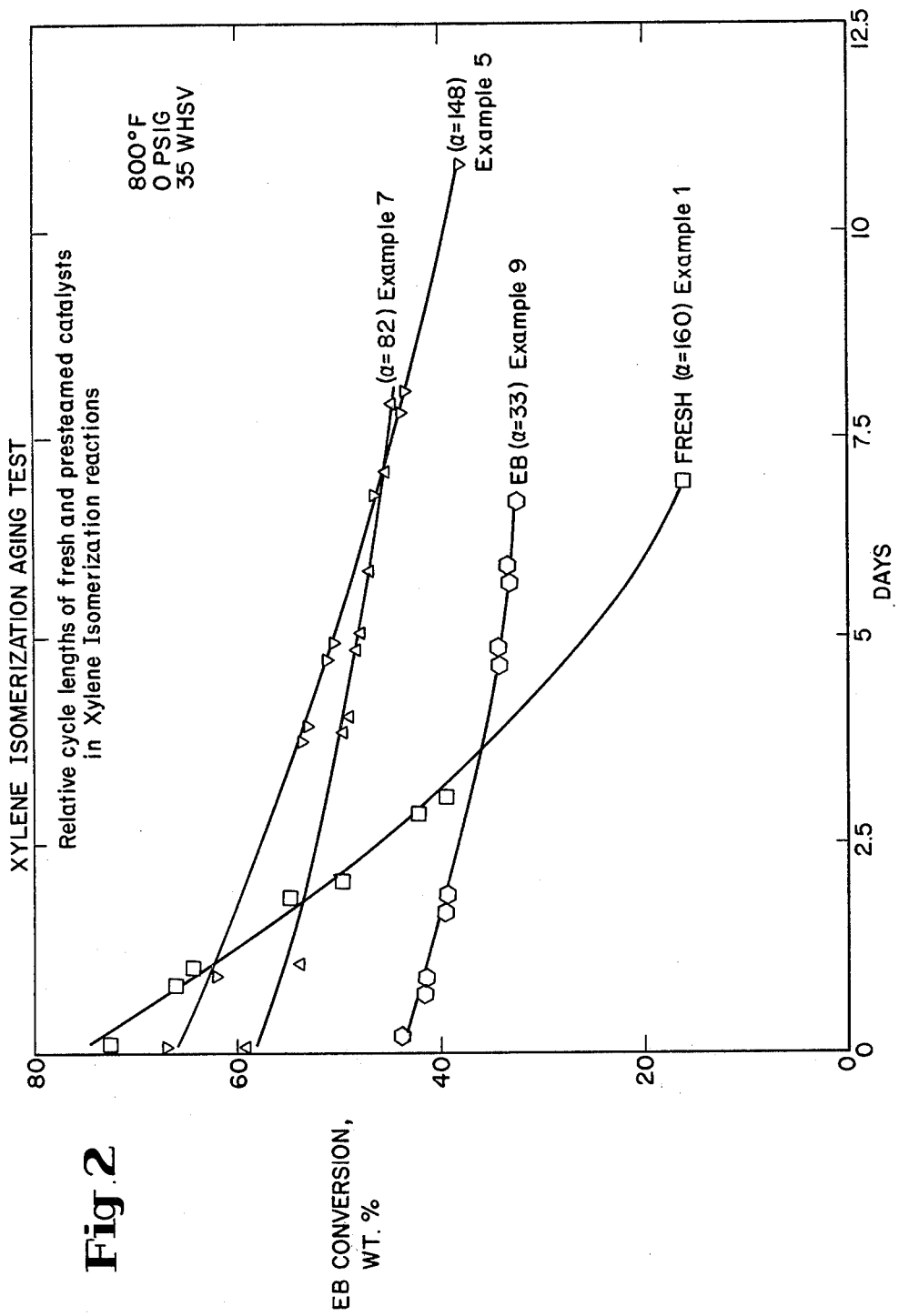

Table 2 and FIG. 1 show the effect of mildly presteaming a zeolite catalyst, e.g., HZSM-5, silica/alumina ratio 40. Such a catalyst is desirable for the conversion of propane to aromatics.

TABLE 2

| | Effect of Presteaming HZSM-5 | | | | |
|---|---|---|---|---|---|
| Example No. | 11 | 12 | 13 | 14 | 15 |
| Steam Treat | None | 100% | 100% | 100% | 100% |
| Hours | Fresh | 6 | 6 | 6 | 6 |
| Temp. °F. | Fresh | 300 | 400 | 500 | 600 |
| Press. psig | Fresh | 0 | 0 | 0 | 0 |
| $\alpha$ | 550* | 520 | 540 | 740 | 600 |
| $\alpha/\alpha_o$ | 1 | 0.95 | 1.0 | 1.3 | 1.1 |

*$\alpha_o$

Figure 3:
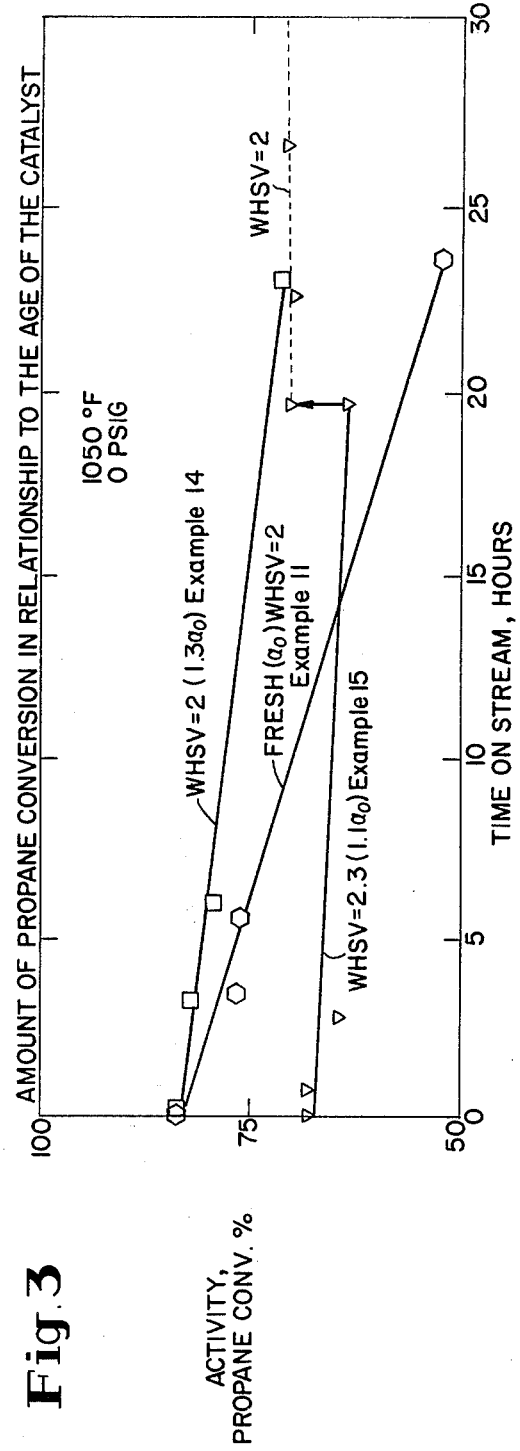

FIG. 3 represents the relationship of the amount of propane conversion to the age of the catalyst (time on stream) for three catalysts illustrated by Examples 11, 14 and 15 of Table 2. The broken curves represent the conversion level (FIG. 3) and selectivity level (FIG. 4) of the optimally steamed catalyst (Example 15) after its WHSV was changed from 2.3 to 2 and the catalyst remained on stream for an additional 20 hours. Although the initial activity of the optimally steamed catalyst was slightly less than that for either the fresh catalyst (Example 11) or the mildly steam treated catalyst (Example 14), the activity of the optimally steamed catalyst showed greater stability than either of the other catalysts.

Figure 4:
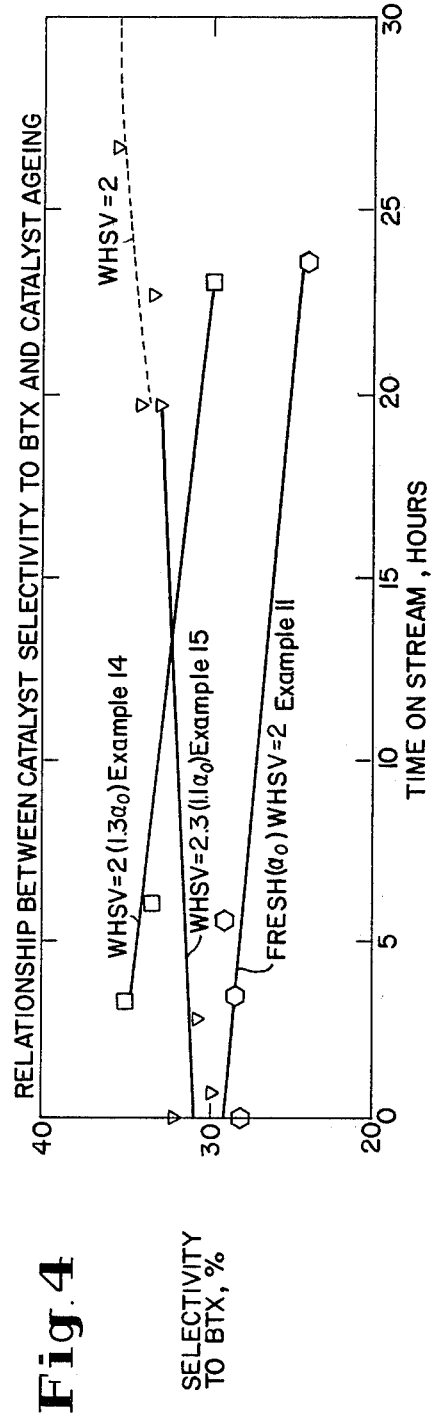

FIG. 4 represents the relationship between catalyst selectivity to BTX and catalyst aging for three catalysts. The selectivity to BTX of the catalyst of Example 15 was greater than that of the fresh catalyst (Example 11). The initial selectivity of the catalyst of Example 14 was slightly greater than the optimally steamed catalyst of Example 15, however, the optimally steamed catalyst shows a greater stability.

The results of these experiments show that mild presteaming of a catalyst to place its $\alpha$-activity past peak enhancement but no less than 75% and, preferably, within 10% of the initial $\alpha$-activity is essential for a highly stable catalyst of high activity and selectivity.

The zeolite catalysts to be steamed according to the invention are generally those zeolites of at least 12 silica/alumina ratio and a constraint index of 1 to 12 which, in the acid form, have activity to convert about 30% of the ethylbenzene in a mixture thereof with xylenes under the isomerization conditions of the said Morrison U.S. Pat. No. 3,856,872, say 600°–700° F. The degree of steaming shall be such that the $\alpha$-activity of the steamed catalyst shall be less than the $\alpha$-activity of the fresh, unsteamed catalyst but no greater than 25% less than the $\alpha$-activity of the fresh catalyst and preferably no greater than 10%. Under these conditions, the reaction temperature of xylene isomerization reactions should increase by no more than 25° F. to attain the same ethylbenzene conversion as was observed before steaming. The reaction of the present invention will be conducted at such elevated temperatures, above 600° F., as to realize about 30% conversion of the ethylbenzene in the charge. As the temperature is further increased to and above about 650° F. the reaction of ethylbenzene shifts from disproportionation to dealkylation.

The present invention involves using mild temperature presteaming to partially deactivate the catalyst. The deactivation should be conducted to a level such that the steamed catalyst activity is no less than 75% of the activity of the fresh, unsteamed catalyst and the process requires a maximum 25° F. rise in operating temperature, well below the minimum 50° F. rise referred to in U.S. Pat. No. 4,236,996. Additionally, the mildly presteamed catalyst demonstrate superior stability characteristics while maintaining catalytic activity substantially equivalent to that of fresh, unsteamed catalysts.

The major importance of this development relates to the use of zeolite catalysts, particularly ZSM-5, in acid catalyzed reactions, e.g., xylene isomerization, propane conversion to BTX, toluene disproportionation, hydrocracking, dewaxing, conversion of alcohols to hydrocarbons such as methanol to gasoline and/or olefins, synthesis gas conversion to fuels, conversion of olefins to heavier fuels, etc. Such reactions would preferably incorporate a catalyst with the unique qualities of stability and catalytic activity similar to fresh, unsteamed catalysts.

Although this invention has been described with particular emphasis on ZSM-5 type zeolites, it is to be understood that larger pore zeolites such as faujasite, particularly of the Y type, and mordenite may also benefit from the mild presteaming. These larger pore size materials are particularly suited for use as hydrocracking and dewaxing catalysts. It is noted that these materials are presteamed in the fresh state as opposed to the regenerated or spent state as disclosed in U.S. Pat. No. 4,276,149.

What is claimed is:

1. In an acid-catalyzed reaction using a catalyst comprising a zeolite having a silica/alumina ratio greater than 12 and a constraint index of 1 to 12, the improvement which comprises steaming said zeolite in its fresh state under controlled conditions of temperature, time and steam partial pressure so as to initially increase the α-activity of said catalyst and produce a steamed catalyst having a peak α-activity, and subsequently reduce the α-activity from said peak α-activity to an α-activity substantially the same as the α-activity of said fresh catalyst and no more than 25% below the initial α-activity of said fresh catalyst, said steamed catalyst having enhanced stability over said fresh catalyst.

2. A process according to claim 1 wherein said zeolite is ZSM-5.

3. A process according to claim 1 wherein said catalyst comprises one or more metal promoters.

4. A process according to claim 3 wherein said catalyst has said metal promoters included on it prior to the steaming procedure.

5. A process according to claim 3 wherein said catalyst has said metal promoters included on it after the steaming procedure.

6. A process according to claim 1 wherein said silica/alumina ratio is no less than 20.

7. A process according to claim 6 wherein said silica/alumina ratio is about 40.

8. A process according to claim 6 wherein said silica/alumina ratio is about 70.

9. In a process for isomerizing the xylene content of a charge mixture of eight carbon atom aromatic hydrocarbon compounds which mixture contains xylenes and ethylbenzene by contact at conversion conditions with a catalyst comprising a zeolite having a silica/alumina ratio greater than 12 and a constraint index of 1 to 12, the improvement which comprises using as said catalyst a steamed zeolite and maintaining a conversion temperature of about 500° F. to about 1000° F., said zeolite having been steamed prior to said contact at a temperature and pressure and for a period of time so as to initially increase the α-activity of said catalyst and produce a steamed catalyst having a peak α-activity, and subsequently reduce the α-activity from said peak α-activity to an α-activity substantially the same as the α-activity of said fresh catalyst and no less than 75% of the initial α-activity of the fresh, unsteamed zeolite, said steamed catalyst having enhanced stability over said fresh catalyst.

10. A process according to claim 9 wherein said zeolite is ZSM-5.

11. A process according to claim 9 wherein said catalyst comprises one or more metal promoters.

12. A process according to claim 9 wherein said catalyst has said metal promoters included on it prior to the steaming procedure.

13. A process according to claim 9 wherein said catalyst has said promoters included on it after the steaming procedure.

14. A process according to claim 9 wherein the reaction temperature is 550° F. to 900° F.

15. A process according to claim 9 wherein said charge mixture comprises at least 5–45% ethylbenzene and 10–75% m-xylene with the remainder of said charge mixture comprising p-xylene, o-xylene, other aromatics and non-aromatics.

* * * * *